United States Patent [19]
Patat et al.

[11] Patent Number: 5,589,462
[45] Date of Patent: Dec. 31, 1996

[54] METHOD OF PREPARING A BIOLOGICAL ADHESIVE ENRICHED WITH PLATELET FACTORS, AND APPLICATION

[75] Inventors: Jean-Louis Patat, Paris; Olivier Delmas, Montbazon; Roland Schmitthaeusler, Montigny-le-Bretonneux, all of France

[73] Assignee: Inoteb, Saint-Gonnery, France

[21] Appl. No.: 244,253

[22] PCT Filed: Sep. 30, 1993

[86] PCT No.: PCT/FR93/00954

§ 371 Date: Jul. 15, 1994

§ 102(e) Date: Jul. 15, 1994

[87] PCT Pub. No.: WO94/07548

PCT Pub. Date: Apr. 14, 1994

[30] Foreign Application Priority Data

Sep. 30, 1992 [FR] France .................................. 92 11643

[51] Int. Cl.⁶ .......................... A61K 38/18; A61K 35/16; C07K 14/49; C07K 1/30
[52] U.S. Cl. .......................... 514/21; 530/351; 530/380; 530/829; 530/830; 424/484; 424/85.1
[58] Field of Search ................... 530/380, 381, 530/382, 364, 829, 830, 351; 514/21; 424/484, 85.1; 106/124

[56] References Cited

U.S. PATENT DOCUMENTS

| | | | |
|---|---|---|---|
| 4,167,823 | 9/1979 | Kumming | 434/262 |
| 4,427,650 | 1/1984 | Stroetmann | 424/46 |
| 4,427,651 | 1/1984 | Stroetmann | 424/46 |
| 4,442,655 | 4/1984 | Stroetmann | 53/428 |
| 4,627,879 | 12/1986 | Rose et al. | 106/124 |
| 4,760,131 | 7/1988 | Sundsmo et al. | 530/356 |
| 4,963,657 | 10/1990 | Pixley | 530/388.25 |
| 5,030,215 | 7/1991 | Morse et al. | 604/410 |
| 5,185,001 | 2/1993 | Galanakis | 604/5 |
| 5,219,328 | 6/1993 | Morse et al. | 604/49 |
| 5,260,420 | 11/1993 | Burnouf-Radosevloh et al. | 530/382 |
| 5,318,782 | 6/1994 | Weis-Fogh | 424/529 |

FOREIGN PATENT DOCUMENTS

| | | |
|---|---|---|
| 0068048 | 1/1983 | European Pat. Off. . |
| 0305243 | 3/1989 | European Pat. Off. . |
| 2448900 | 9/1980 | France . |
| 2041942 | 9/1980 | United Kingdom . |
| 86/03122 | 6/1986 | WIPO . |
| 88/03409 | 5/1988 | WIPO . |
| 89-05656 | 6/1989 | WIPO . |
| 91/09573 | 7/1991 | WIPO . |
| 92/09301 | 6/1992 | WIPO . |

OTHER PUBLICATIONS

Deuel et al. "Human Platelet–Derived Growth Factor" J. Biol. Chem. 256(17) 8896–8899, 1981.

Ochsner et al. "Fibrin Glue as a Hemostatic Agent in Hepatic & Splenic Trauma" J. Trauma 30(7):884–887, 1990.

*Primary Examiner*—John L. LeGuyader
*Assistant Examiner*—Nancy J. Degen
*Attorney, Agent, or Firm*—Oliff & Berridge

[57] ABSTRACT

A method for the preparation of a platelet factor-enriched biological adhesive comprising freezing a platelet-enriched plasma and isolating a cryoprecipitate from the frozen platelet-enriched plasma is disclosed. Also disclosed is a method for biological adhesion employing the prepared biological adhesive.

16 Claims, No Drawings

METHOD OF PREPARING A BIOLOGICAL ADHESIVE ENRICHED WITH PLATELET FACTORS, AND APPLICATION

The subject of the invention is the production of a biological adhesive containing coagulable human plasma proteins. The biological adhesive obtained according to the invention contains especially growth factors of platelet origin.

It is known that concentrates of thrombin-coagulable proteins, or fibrinogen solutions, are used in the production of an adhesive material which makes it possible especially to join living tissues while exerting a haemostatic action; see for example Patent FR-2,448,900. This adhesive material is commonly called "biological adhesive" and is used in surgery.

Biological adhesives make it possible to reproduce, under physiological conditions, the final phase of the coagulation process. For that, a solution containing fibrinogen and factor XIII are mixed, immediately before use, with a solution containing thrombin and calcium ions on living tissue to be treated. Fibrinogen, in the presence of thrombin and calcium ions, is converted to fibrin. The fibrin monomers join together to form fibrin polymers and these polymers are cross-linked by the action of activated factor XIII. Factor XIII, activated under the action of thrombin in the presence of calcium ions, is a transamidase which forms peptide bonds between the fibrin chains with formation of a network.

In the present application, the name "biological adhesive" will refer to a concentrate of thrombin-coagulable proteins, although in fact it is only in the presence of thrombin and calcium salts (or after activation of the prothrombin which it contains) that such a concentrate truly constitutes an adhesive.

The formation of the network of fibrin is responsible for the haemostatic activity of the biological adhesive. Moreover, fibrin adheres to the surrounding tissues, especially through fibronectin and collagen. In addition, activated factor XIII forms peptide bonds fibrin and fibronectin, thereby reinforcing the adhesive properties.

It is known that fibrin clot disappears gradually, in vivo, under the action of a proteolytic enzyme called plasmin, thereby limiting the duration of the adhesive bonding. It is however possible to reinforce the duration of action of biological adhesives by supplementing them for example with alpha-2-antiplasmin or a protease inhibitor such as aprotinin, or alternatively epsilon-aminocaproic acid.

The applications of biological adhesives are numerous, in particular in surgery for avoiding bleeding, for replacing suture threads or for reinforcing sutures.

However, biological adhesives do not have a specific activity capable of promoting cicatrization.

It is known that cicatrization is promoted especially by certain growth factors acting directly on target cells present in the wound. These growth factors induce multiplication or differentiation, or even cell attraction (chemotactism). Blood platelets (or thrombocytes) are one of the principal sources of growth factors in blood.

During a cellular lesion in vivo, the thrombocytes liberate the growth factors contained in granules, under the action of thrombocyte activators, including thrombin. The supernatants of activated platelets contain a great diversity of molecules, such as for example platelet-derived growth factor or PDGF, transforming growth factor beta, basic fibroblast growth factor, platelet factor 4, platelet-derived endothelial growth factor, heparin-binding epidermal growth factor, insulin-like growth factor 1, connective-tissue activating peptide III, beta-thromboglobulin, epidermal growth factor, plasminogen, Von Willebrand factor, fibrinogen, serotonin, histamine, adenosine di- and triphosphate, fibronectin, vitronectin, platelet factor XIII, proteolytic or glycolytic enzymes, metabolites of arachidonic acid and the like; see especially H. L. Wong & S. M. Wahl, in "Peptide Growth Factors and their Receptors" Sporn & Roberts Eds., Springer-Verlag. Berlin, p. 510; R. A. Terkeltaub & M. H. Ginsberg, in "The Molecular and Cellular Biology of Wound repair", Clark & Henson Eds., Plenum Press, New York, p. 38.

Platelets extracts contain a high mitogenetic activity, and their cicatrizing effect is known; see especially D. Knighton et al., Ann. Surg., 196, 379–388 (1982); D. M. Carter et al., in "Growth factors and other aspects in Wound Healing", Barbul. Pines, Cadwell Hunt Eds, Alan R. Liss Inc., New York 1988, p. 303–317; U.S. Pat. No. 4,760,131 and PCT Patent Applications WO 86/03122, WO 88/03409 and WO 89/05656.

It has now been discovered that it is possible to obtain an improved biological adhesive, promoting especially cicatrization, by virtue of a method which makes it possible to join both thrombin-coagulable proteins and platelet factors.

The modes of preparation of concentrates of thrombin-coagulable proteins are known. The raw material consists of blood plasma, that is to say blood from which the blood cells have been removed. In other words, it is a product depleted of platelets. The method consists essentially in precipitating fibrinogen either with ethanol, according to the Cohn method, or by the production of a cryoprecipitate. It is known that the preparation of a cryoprecipitate consists in freezing a plasma and then in thawing it at a temperature greater than 0 and less than 6° C., generally between +1° and +4° C. The solid fraction which remains, and which contains especially fibrinogen and fibronectin, is called cryoprecipitate and can be separated from the liquid fraction by centrifugation. The volume of cryoprecipitate is generally between 1/25 and 1/100 of the volume of initial plasma. The plasma proteins which are insoluble under the conditions of production of the cryoprecipitate are therefore concentrated by a factor of 25 to 100 during the cryoprecipitation. But the preparations thus obtained are low in growth factors. In particular, the biological adhesives prepared according to known industrial processes do not contain notable mitogenetic activity.

It has now been discovered that by using, as initial product, a platelet-enriched plasma, numerous platelet factors, although normally soluble under the conditions for production of the cryoprecipitate, become retained in the said cryoprecipitate in very high proportions, when a uniform distribution of these factors between the liquid fraction and the cryoprecipitate which are obtained would normally be expected.

The method of the invention makes it possible to obtain a product combining the haemostatic and adhesive properties of concentrates of thrombin-coagulable proteins and the cicatrizing activies of platelet extracts, without it being necessary to carry out two separate preparations.

Thus, by virtue of the method of the invention, the PDGF concentration factor, in the cryoprecipitate, is generally greater than 10. The PDGF yield is generally greater than 20 ng per billion platelets present in the initial plasma.

The subject of the invention is therefore a biological adhesive containing a concentrate of thrombin-coagulable proteins, characterized by the fact that it contains at least one growth factor of platelet origin.

The said growth factor is especially PDGF.

The biological adhesive obtained according to the invention generally contains at least 20 ng/ml, and most often at least 50 ng/ml of PDGF. Generally, it can contain 20 to 600 ng/ml of PDGF.

The biological adhesive according to the invention contains other products normally present in platelet extracts, and in particular beta-thromboglobulin, type 1 inhibitor of plasminogen activator (PAI-1) and platelet factor XIII (factor XIII-A). It contains for example at least 10 μg/ml, and in particular 10 to 300 μg/ml, of beta-thromboglobulin, at least 1 μg/gl of PAI-1 and in particular 5 to 40 μg/ml, of PAI-1. The proportion of factor XIII-A relative to factor XIII-S is at least 1.2 times higher than the proportion of these factors in a normal plasma, and in particular 1.2 to 4 times higher.

The biological adhesive of the invention contains for example:

proteins: 60–200 g/l, fibrinogen: 30–150 g/l, in particular 50–100 g/l, fibronectin: 6–14 g/l, especially 8–12 g/l, factor XIII: 10–60 plasma equivalent units, albumin: 10–38 g/l, in particular 18–30 g/l.

Plasma equivalent unit corresponds to the normal plasma concentration of factor XIII present in a pool of plasmas.

The concentration of proteins is determined by the Biuret method. The concentration of fibrinogen is determined by the gravimetric method, the concentration of fibronectin and PAI-1 by an ELISA test (Stago), according to the instructions of the manufacturer, the factor XIII activity by a test ammonia liberation caused by the incorporation of glycine ethyl ester in a peptide substrate (Berichrom F XIII reagents, Behring), according to the recommendations of the manufacturer, factors XIII-A and XIII-S by the Laurell method using specific antisera (Stago). The concentration of albumin is determined by electrophoresis on cellulose acetate (Sebia), according to the recommendations of the manufacturer. The protein content of the electrophoresis band characteristic for albumin is determined by densitometry.

The biological adhesive of the invention contains coagulation factors in sufficient quantity to confer on it the property of coagulating by activating either the intrinsic route for the coagulation, or the extrinsic route for the coagulation. The biological adhesive contains for example between 0.5 and 1.5 times the normal plasma concentration of prothrombin, determined either by the Laurell method using a specific antiserum (Stago) or the chronometric method (Stago deficient II, Stago), according to the recommendations of the manufacturer.

A ½ dilution, in a physiological buffer, of the biological adhesive has a Quick time equivalent to that of a normal plasma diluted between ½ and ⅙. The Quick time explores the capacity to activate the extrinsic route for the coagulation. It is determined with the aid of the reagent of trademark "Neoplastine" (Stago), containing thromboplastin, according to the recommendations of the manufacturer.

A ½ dilution, in a physiological buffer of the biological adhesive has a Kaolin time equivalent to that of a normal plasma diluted between 1:1 and 1:4. The Kaolin time explores the capacity for activation of the intrinsic route for the coagulation. It is determined with the aid of the C. K. PREST reagents (Stago), according to the recommendations of the manufacturer, except that cephalin is omitted during the carrying out of the test.

The biological adhesive according to the invention contains platelet factors in sufficient quantity to confer on it mitogenetic properties, which can be demonstrated according to conventional methods.

The mitogenetic activity of the biological adhesive according to the invention is for example such that diluted ¼₀₀₀ (and even, generally, ⅕₀₀₀), it has a mitogenetic activity at least equal to that of a solution containing 0.1 ng/ml of PDGF in a test for the measurement of the incorporation of tritiated thymidine by 3T3 cells stimulated to a growth-stopping phase.

Such a test is described for example by HART C. E. et al., Biochemistry vol. 29, 166–172 (1990).

The 3T3 cell is a Swiss mouse embryo cell (line ATCC CCL 92). A line obtained from a subcloning is also available (NIH/3T3; ATCC CRL 1658).

The biological adhesive according to the invention may essentially consist of a cryoprecipitate derived from a platelet-enriched plasma, and the invention relates to a method for preparing a biological adhesive in which a cryoprecipitate is prepared and collected from a frozen plasma, characterized by the fact that a platelet-enriched plasma is used as initial plasma.

In other words, the method of the invention is characterized by the fact that before preparing the cryoprecipitate, a platelet-enriched plasma is prepared. The operation for enriching the plasma with platelets is carried out according to the customary methods, especially by centrifugation of the blood collected.

The platelet-enriched plasma also contains at least 50 million platelets per ml, especially about 100 million to 1 billion platelets per ml, and for example about 100 million to 500 million per ml.

The conditions for production of the cryoprecipitate are the conventional conditions. For example, the freezing is carried out at a temperature not greater than −15° C., for example between −15° and −60° C. The product is maintained at this temperature for at least a time sufficient to allow a thermal equilibrium in the product mass. This time is for example of the order of 12 hours to 72 hours.

The plasma is then thawed at a temperature greater than 0° C. but less than the temperature at which the whole frozen product liquefies. The procedure is generally carried out at between +1° and +6° C. and in particular at around +4° C. The duration of incubation at the thawing temperature is sufficient to allow a thermal equilibrium to be achieved; this duration is for example between 12 and 24 hours.

The cryoprecipitate can then be separated from the liquid fraction. For that, the thawed plasma is centrifuged at a sufficiently high temperature so as not to re-freeze it, and sufficiently low to avoid liquefaction of the cryoprecipitate, and then the supernatant is removed according to known methods, and the cryoprecipitate which constitutes the centrifugation pellet is recovered. The volume of the cryoprecipitate generally represents ¹⁄₂₅th to ¹⁄₁₀₀th of the initial plasma volume.

Generally, the centrifugation is carried out at a temperature of between +1° and +6° C.

In the case where it is not desired to immediately use the biological adhesive consisting of the cryoprecipitate obtained, it can be re-frozen, for example at −20° C.

When the biological adhesive is intended to be used immediately, it is advisable to liquefy it by heating to a sufficient temperature, usually between 32° and 38° C.

The simplicity of the method of producing the platelet factor-enriched biological adhesive according to the invention makes it possible to apply this method to the production of an autologous biological adhesive, that is to say obtained from plasma derived from one donor, for use in this donor. One of the advantages of this method is that all the operations, including the enrichment of the plasma with platelets, can be carried out in a system of bags used for the collection of blood from a donor.

The biological adhesive can of course be also prepared from plasma derived from several identified donors.

The initial product of the method of the invention is a platelet-enriched plasma. The preparation of such platelet-enriched plasma is known per se. It can be produced for example according to the following method. Whole blood, collected during a blood donation, in a triple bag system (for example Maco-pharma), is centrifuged in a Jouan K110 centrifuge at 3000×g for 4 minutes. The supernatant plasma, rich in platelets, is poured into the transfer bag 3 of the triple bag system, with the aid of a plasma extractor. The bag 3 is separated from the rest of the system by sealing the tube. It is this bag which will be used for the manufacture according to the invention of the concentrate of thrombin-coagulable proteins.

The subject of the invention is also the use of the biological adhesive which can be obtained according to the abovementioned method.

This use can be implemented according to methods known per se. The principle of this use consists in causing the formation of fibrin by conversion of fibrinogen. This conversion is performed by the action of thrombin. The thrombin may be exogeneous thrombin added, according to methods known per se: for that, the biological adhesive obtained as described earlier is mixed with an aqueous solution containing thrombin and calcium ions so as to initiate the coagulation reaction by conversion of fibrinogen to fibrin.

There may be used especially an aqueous solution containing 0.5 to 500 NIH U/ml of thrombin and a calcium ion (especially in the form of calcium chloride) concentration for example of between 5 and 100 mM, in particular between 20 and 60 mM.

The mixing with the thrombin solution is preferably carried out in situ, on the tissues to be treated.

Generally, the liquefied cryoprecipitate and the aqueous thrombin solution are mixed in proportions by volume of 5:1 to 1:2.

If desired, a plasmin inhibitor or an analogue (for example alpha-2-antiplasmin, aprotinin, epsilon-aminocaproic acid or tranexamic acid) is added to the final adhesive, or to one of its constituents before they are mixed.

Advantage can also be favourably taken of the presence of prothrombin and of other coagulation factors in the biological adhesive of the invention, and either the extrinsic route, or the intrinsic route for the coagulation can be activated.

The subject of the invention is therefore especially the use of the biological adhesive obtained as indicated earlier, this use being characterized by the fact that at least one agent favouring the activation of endogeneous prothrombin is added to the said biological adhesive. The coagulation phenomenon is also initiated by carrying out the procedure preferably at a temperature close to 37° C.

For that, an aqueous solution containing calcium ions (for example 5–100 mM, in particular 20–60 mM) simply has to be added to the biological adhesive.

If it is desired to accelerate this coagulation, the procedure can be carried out as indicated below, with the aid of activators.

To activate the intrinsic route, it is possible to mix the biological adhesive with an aqueous solution containing calcium ions (for example 5–100 mM, in particular 20–60 mM), and to bring it into contact with at least one known activator of coagulation factor XII, and more generally with solid surfaces or compounds, for example in powder form, which are insoluble in the biological adhesive and have negative charges, such as silicates, (especially Kaolin), silica, silica glass, crystals of calcium carbonate, such as for example aragonite, obtained for example from coral skeletons, or crystals of tricalcium dicitrate. After a sufficient time, which can be determined by simple routine experiments, the biological adhesive is separated from the said insoluble compounds by filtration. The procedure can for example be carried out in a column provided with a filter.

To activate the extrinsic route for the coagulation, it is possible to mix the biological adhesive with an aqueous solution containing calcium ions (5–100 mM, in particular 20–60 mM) and tissue thromboplastin, for example of animal origin, or thromboplastin produced by genetic engineering.

One of the important advantages of the biological adhesive obtained according to the invention is therefore that it contains prothrombin in sufficient quantity to allow initiation of the coagulation of the adhesive without addition of exogeneous thrombin, thereby reducing the risks of accidental contamination. The method of the invention is therefore particularly adapted to the current needs for the use of autologous products.

The biological adhesive according to the invention can be used especially in the treatment of traumatic or surgical wounds, in the fitting and holding of grafts (especially skin or bone grafts or the like). It can also be used for fixing prosthesis parts, including bone prostheses, osteosynthesis parts and dental prostheses, and also for fixing and holding together bone filling materials, especially resorbable filling materials based on calcium carbonate (for example based on coral skeleton or *Pinctada margaritifera shell*), hydroxyapatite or biodegradable polymers such as poly(lactic acid).

EXAMPLE 1

A platelet-enriched human plasma is prepared as described earlier.

The enriched plasma thus obtained contains 154 million platelets per ml.

The transfer bag containing 230 ml of the said platelet-enriched plasma is placed in a cold chamber at −40° C. for 72 hours. The plasma bag is then placed in a refrigerator at a temperature of 4° C. for 20 hours. The plasma bag is then centrifuged for 20 minutes at 3,000 revolutions per minute, still at the temperature of +4° C. After centrifugation, the bag is placed horizontally, a sampling tube is fitted and the liquid supernatant is drawn off by aspiration.

The solid residue contained in the bag constitutes the cryoprecipitate which can be preserved by refreezing at a temperature of −20° C. until it is used.

When it is desired to use the cryoprecipitate immediately, the bag is placed in a water bath, for example at a temperature of 37° C. After incubating for 15 minutes, the residual solution is collected. Its volume is about 3 ml.

Analysis of the product obtained: see Table I below.

EXAMPLE 2

The procedure is carried out in a manner similar to that described in Example 1. The volume of treated plasma is 250 ml. The plasma initially contained 256 million platelets per ml. The volume of the final solution recovered, derived from the liquefaction of the cryoprecipitate, is 5 ml.

Analysis: see Table I.

The PDGF content of the supernatant obtained after centrifugation of the thawed plasma is only 5.9 ng/ml.

It can be seen (by comparison with Table I) that practically all the PDGF is in the cryoprecipitate.

TABLE I

|  | Example 1 | Example 2 |
|---|---|---|
| Proteins (1) (mg/ml) | 61 | 89.6 |
| PDGF (2) (ng/ml) | 282 | 310 |
| Beta-thromboglobulin (3) (µg/ml) | 127 | 130 |
| Coagulable by thrombin (4) | YES | YES |
| Mitogenetic activity (5) (specific activity) | 104 | not measured |

(1) Determined by the Bradford method (Biorad reagent reference 500-0006)
(2) PDGF: platelet-derived growth factor, measured by an "ELISA" test
(3) Measured by an "ELISA" test (Stago, France, reference 0419)
(4) Determined by mixing one volume of liquefied cryoprecipitate with one volume of a solution of thrombin at 500 NIH U and 50 mM calcium chloride. After 1 minute, the formation of a clot is observed.
(5) The specific activity is determined according to the procedure described below. The radioactivity obtained with the control is 2000 cpm. At 4000 cpm, the protein concentration is 0.0096 mg/ml in Example 1. As a guide, the specific activity of Tissucol (trademark designating a biological adhesive sold by IMMUNO) measured by the method, is 0.22.

The procedure for the measurement of the mitogenetic activity was the following:

Fibroblast cells are isolated from the prepuce of a 6-month old child.

The cells are suspended in DMEM medium (Gibco) containing 10% foetal calf serum. Each well of a 96-well microtitre plate is inoculated with 200 µl of the suspension at 40,000 cells per ml. After incubating for 3 days at 37° C., under an atmosphere containing 5% of $CO_2$, the culture medium is replaced with a DMEM medium (Gibco) containing 8% newborn calf serum.

After incubating for an additional 3 days, 50 µl of a solution of thrombin-coagulable proteins (sample) are added. Each sample is tested at various dilutions in DMEM, and in triplicate. 50 µl of DMEM are inoculated into control wells. The microplate is incubated under the same conditions for 24 hours. Six hours before the end of the incubation, 50 µl of a solution of tritiated thymidine at 10 µCi/ml are added to each well. After the incubation, the wells are washed with a physiological solution. The cells are then detached from the well by a trypsin solution at 0.25%, in the presence of ethylene-diaminetetraacetate (Gibco solution). The cells are harvested on a filter, by means of a "Skatron" type cell collector. The filters are then dried and the radioactivity is measured in the presence of a scintillation liquid.

Determination of the Specific Activity

The protein concentration of the sample in the well (expressed in mg/ml) is plotted on a graph, on the x-axis and the corresponding radioactivity on the y-axis. The protein concentration of the sample which gives a radioactivity level twice that of the control wells is graphically determined by interpolation. The reciprocal of this concentration is called the specific activity of the sample.

EXAMPLE 3

The procedure is carried out in a manner similar to that of Example 1. The results of the analyses (mean values for several experiments) are presented in Table II.

TABLE II

| Concentration of platelets in the initial plasma | No. of exp. | Mean | Min. val. | Max. val. |
|---|---|---|---|---|
| $10^6$/ml | 15 | 350 | 221 | 552 |
| Proteins g/l | 15 | 120 | 95 | 160 |
| Fibrinogen g/l | 15 | 69 | 52 | 93 |
| Fibronectin g/l | 9 | 7.8 | 6 | 13 |
| Factor XIII PEU* | 15 | 28 | 15 | 57 |
| F XIII-A/F XIII-S | 4 | 2.9 | 2.14 | 3.7 |
| PDGF ng/ml | 4 | 400 | 300 | 600 |
| beta-thromboglobulin µg/ml | 9 | 200 | 184 | 250 |
| Albumin g/l | 6 | 25.1 | 19.8 | 35.9 |
| PAI-1 µg/ml | 5 | 19 | 14 | 24 |

*PEU: plasma equivalent unit

EXAMPLE 4

A biological adhesive is prepared in a manner similar to that described in Example 1. In a tube, there are successively mixed 150 µl of biological adhesive, 150 µl of physiological saline, 300 µl of aqueous calcium chloride solution at 25 mM and, either 300 µl of a suspension of Kaolin, or 300 µl of a suspension of coral powder, or 300 µl of physiological saline. The tube is incubated at 37° C. on a water bath. The appearance of a coagulum in the tube is monitored.

In the presence of Kaolin, the coagulum forms after 4 minutes of incubation. In the presence of coral powder instead of Kaolin, the coagulum forms in 7 min. The preparation without Kaolin or coral (obtained simply by addition of physiological saline) coagulates after 9 min.

We claim:

1. A method of preparing a platelet factor-enriched biological adhesive, comprising:

(a) freezing a platelet-enriched plasma; and (b) isolating a cryoprecipitate from the frozen platelet-enriched plasma.

2. The method according to claim 1, wherein said platelet enriched-plasma contains at least 50 million platelets per ml.

3. The method according to claim 2, wherein said platelet-enriched plasma contains 100 million to 1 billion platelets per ml.

4. The method according to claim 2, wherein said platelet-enriched plasma contains 100 million to 500 million platelets per ml.

5. The method according to claim 1, wherein said cryoprecipitate is heated in order to obtain said adhesive in liquid form.

6. The method according to claim 1, wherein said platelet-enriched plasma is prepared from collected blood.

7. The method according to claim 6, wherein said collected blood is obtained from one donor, and all steps of said method are carried out in a system of bags used for collecting blood.

8. The method according to claim 1, wherein a yield of at least 20 ng of platelet-derived growth factor (PDGF) per billion platelets in an initial volume of said platelet-enriched plasma is obtained.

9. The method according to claim 1, wherein said cryoprecipitate comprises PDGF at a concentration that is more than 10 times greater than a plasma concentration of PDGF in said platelet-enriched plasma prior to said method.

10. A biological adhesion method comprising connecting at least two surfaces with a platelet facton-enriched biological adhesive obtained by isolating a cryoprecipitate prepared from a frozen platelet-enriched plasma.

11. The method according to claim 10, wherein said adhesive further comprises an agent which promotes activation of endogeneous prothrombin.

12. The method according to claim 11, wherein said agent is an aqueous solution containing calcium ions.

13. The method according to claim 11, wherein said agent comprises thromboplastin and calcium ions.

14. The method according to claim 11, wherein said agent comprises an activator of coagulation factor XII and calcium ions.

15. The method according to claim 14, wherein said activator is chosen from solid compounds which are insoluble in the biological adhesive and have negative charges.

16. The method according to claim 15, wherein said solid compound is at least one member selected from the group consisting of silicates, silica glass, calcium carbonate and tricalcium dicitrate.

* * * * *